US00PP10896P

United States Patent [19]

Wain

[11] Patent Number: Plant 10,896

[45] Date of Patent: May 11, 1999

[54] CHRYSANTHEMUM PLANT NAMED 'PARTY TIME'

[75] Inventor: Peter Wain, V.R. Portsmouth, United Kingdom

[73] Assignee: Cleangro, Ltd., West Sussex, United Kingdom

[21] Appl. No.: 08/936,965

[22] Filed: Sep. 25, 1997

[51] Int. Cl.[6] ..... A01H 5/00

[52] U.S. Cl. ..... Plt./288

[58] Field of Search ..... Plt./77, 288

[56] References Cited

U.S. PATENT DOCUMENTS

P.P. 6,613 2/1989 Duffett et al. ..... Plt./77
P.P. 6,680 3/1989 Jordan, et al. ..... Plt./77

*Primary Examiner*—Howard J. Locker
*Attorney, Agent, or Firm*—Christie, Parker & Hale, LLP

[57] ABSTRACT

A new plant variety of Chrysanthemum producing white flowers.

1 Drawing Sheet

BACKGROUND OF THE INVENTION

The present invention is directed to a new and distinct variety of Chrysanthemum botanically classified as *Dendranthema grandiflora*. The varietal denomination of the new chrysanthemum is 'Party Time'.

The female parent of the new variety is an undistributed, unpatented seedling identified as p 79-5 and the male parent is the variety known as 'Fashion Time' (U.S. Plant Pat. No. 9,935). The new variety has been asexually reproduced by vegetative cuttings in Ventura County, Calif. and the distinguishing characteristics are retained through successive generations of asexual reproduction.

SUMMARY OF THE INVENTION

'Party Time' is a pot forcing chrysanthemum plant variety that produces white flowers and dark green foliage and has a flat capitulum form and flower size of about 9 cm across.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of October. 'Party Time' has not been observed under all possible environmental conditions. The phenotype may vary with variations in the environment such as temperature, light intensity, day length and cultural conditions. The color description is by reference to The Royal Horticultural Society Colour Chart.

Plants of the new variety have been grown successfully in a greenhouse under temperature conditions averaging about 65° F. at night and about 75 –85° F. during the day under light conditions of about 5,000–6,000 foot candles. To produce a commercial product the plants may be pinched once center bud removed. It has been observed that the shelf life of 'Party Time' is about 29 days with the response time of about 9 weeks.

Plant

Habit: Upright branching.
Height: About 26 cm.

Branching characteristics: Very good brancher.
Number of breaks from pinch: About 4 per.
Typical container size to be grown in: 4", 5", 6", 8", 10".
Length of lateral branches: Average— about 15 cm.
Stem color: Near 144A.

Foliage

Leaf arrangement: Alternate.
Number of leaves per lateral branch:
*Average number leaves per lateral branch.*—About 6 fully mature leaves and 6 immature leaves.
(1) Size: Length— Average about 6.1 cm. Width — Average about 3.9 cm.
(2) Shape: Obovate.
(3) Attachment: Petiole.
(4) Apex: Obtuse with serration at tip.
(5) Base: Tapered.

| (6) | Color: | Mature | Young |
|---|---|---|---|
| | Top: | Near 137B | Near 137A |
| | Bottom: | Near 137B | Near 138B |

Margin: Few fine serrations.
Aspect: Very slight undulation.
Surface characteristics:
*Top.*—Tomentose.
*Bottom.*—Puberulent.
Petiole:
(1) *Length.*—About 1.5 cm.
(2) *Color.*—Near 144B.
(3) *Other Characteristics.*—Winged, 2 to 4 stipule-like attachments at base, about 2 per mature leaf; many lobed, acute tips, attached to stem and petiole.
Stipule: Rarely present, when present average 0.2 cm in width.

Flower

Inflorescence form: Cyme.
Flower form: Decorative.
Flower shape: Circular.
Flower color (general): White with slight yellow center, near 8D.
Blooms: About 4 blooms average per stem.
(1) *Diameter.*—Average about 9 cm.
(2) *Depth.*—Average about 2.1 cm.

(3) *Longevity on plant.*—About 29 day shelf life.

Sepal:

(1) *Number.*—About 40.
(2) *Color.*—Near 137C.
(3) *General appearance.*—Very thin, acute tips, slight membranous edges, curved under very slightly.

Peduncle:

(1) *Length.*—Average about 6 cm.
(2) *Habit.*—Upright, curving out slightly.
(3) *Surface.*—Tomentose.
(4) *Color.*—Near 137D.
(5) *Strength.*—Easily bent but not broken because of flexibility.

Bud:

(1) *Shape.*—Sphere with flat top.
(2) *Diameter.*—Avg. about 1 cm.
(3) *Color.*—Near 138B.
(4) *Height.*—About 0.5 cm.

Ray florets:

(1) *Number per flower.*—Average about 380.
(2) *Fused.*—No.
(3) *Texture.*—Matte, slight ripples.
(4) *Shape.*—Elliptic, very narrow.
(5) *Apex.*—3 lobes, irregular depths.
(6) *Base.*—Tapered.
(7) *Margin.*—Entire.
(8) *Aspect.*—Undulating, reflexed back with age, rolled under.
(9) *Length.*—Avg. About 4.6 cm.
(10) *Width.*—Avg. About 1 cm average.

*Color* — top side. —Immature: Near 155B. Mature: Near 155D. Fading: Near 155B.

*Color* — under side.—Immature: Near 155B. Mature: Near 155D. Fading: Near 155B.

Disc florets:

(1) *Number per inflorescence.*—About 5.
(2) *Texture.*—Shiny.
(3) *Shape.*—Cylindric.
(4) *Margin.*—Entire.
(5) *Length.*—About 0.3 cm.
(6) *Width.*—About 0.08 cm.

*Color.*—Immature: Near 17A. Mature: Near 23B. Fading: Near 24B.

*Fragrance.*—Fragrance of entire bloom is musty.

Description of flower as it ages: Ray florets become almost translucent and very loose. Aspect of ray florets very irregularly undulating.

Reproductive Organs

Ray florets:

*Pistillate.*—(1) Pistil number: 1 per floret. (2) Ovary shape: Spherical with steeply domed top. (3) Stigma shape: Short fork curling out. (4) Stigma color: Near 9A. (5) Style length: Average about 0.6 cm. (6) Style color: Near 2C.

Disc florets: Staminate and pistillate.

*Pistillate.*—(1) Stigma shape: Linear. (2) Style length: About 0.1 cm.

*Staminate.*—(1) Stamen number: About 6. (2) Anther length: About 0.2 cm. (3) Anther shape: Linear, tapered to point. (4) Pollen quantity: Scant.

What is claimed is:

1. A new and distinct Chrysanthemum plant of the variety substantially as herein shown and described.

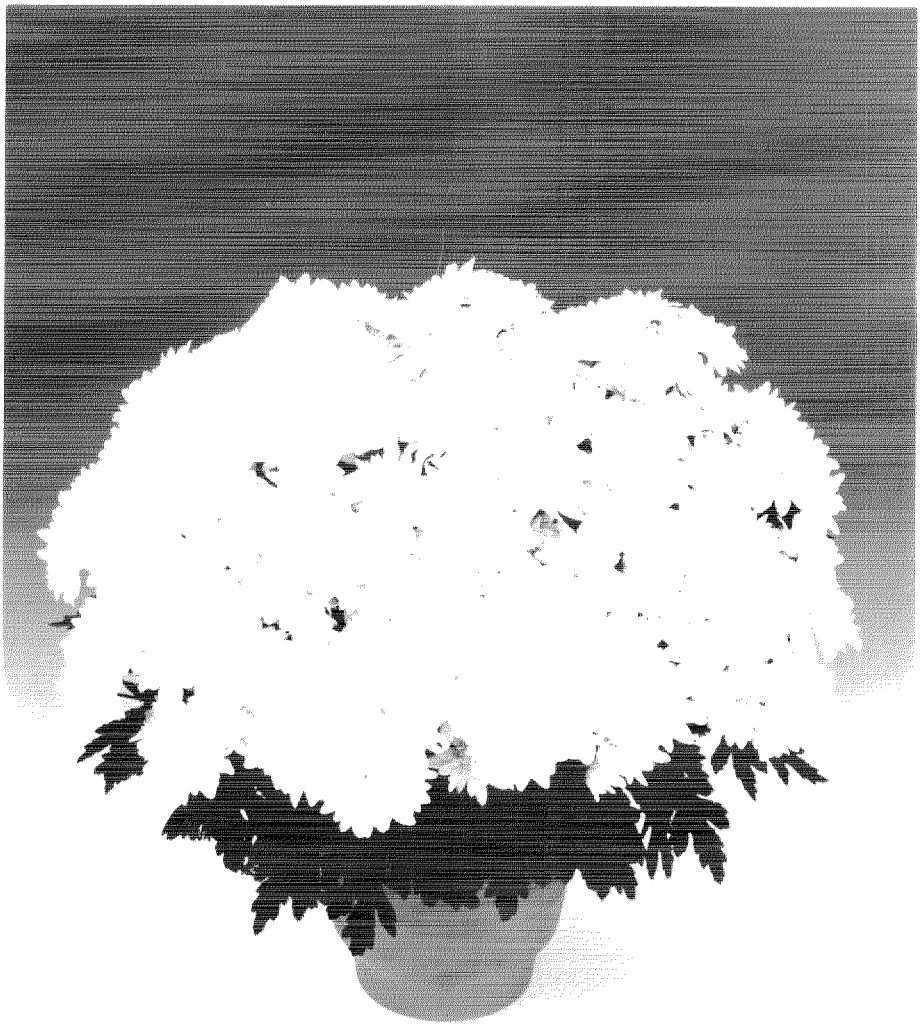

* * * * *